(12) United States Patent
Tognetti et al.

(10) Patent No.: US 11,389,074 B2
(45) Date of Patent: *Jul. 19, 2022

(54) DEVICE, SYSTEM AND METHOD FOR DETECTION AND PROCESSING OF HEARTBEAT SIGNALS

(71) Applicant: Empatica Srl, Milan (IT)

(72) Inventors: Simone Tognetti, Vimodrone (IT); Ivan Cenci, Verucchio (IT); Daniele Resnati, Carate Brianza (IT); Maurizio Garbarino, Turin (IT); Matteo Lai, San Sperate (IT)

(73) Assignee: Empatica Srl, Milan (IT)

( * ) Notice: Subject to any disclaimer, the term of this patent is extended or adjusted under 35 U.S.C. 154(b) by 146 days.

This patent is subject to a terminal disclaimer.

(21) Appl. No.: 16/687,061

(22) Filed: Nov. 18, 2019

(65) Prior Publication Data

US 2020/0323449 A1 Oct. 15, 2020

Related U.S. Application Data

(63) Continuation of application No. 16/371,701, filed on Apr. 1, 2019, now abandoned, which is a continuation
(Continued)

(51) Int. Cl.
*A61B 5/00* (2006.01)
*A61B 5/024* (2006.01)
(Continued)

(52) U.S. Cl.
CPC ........ *A61B 5/02416* (2013.01); *A61B 5/0002* (2013.01); *A61B 5/0071* (2013.01);
(Continued)

(58) Field of Classification Search
CPC .......... A61B 2562/0219; A61B 5/0002; A61B 5/0071; A61B 5/02416; A61B 5/0531;
(Continued)

(56) References Cited

U.S. PATENT DOCUMENTS

| 5,218,207 A | 6/1993 | Rosenthal |
| 7,539,533 B2 | 5/2009 | Tran |

(Continued)

FOREIGN PATENT DOCUMENTS

| CN | 1826747 A | 8/2006 |
| CN | 201005691 Y | 1/2008 |

(Continued)

OTHER PUBLICATIONS

Office Action dated Nov. 12, 2019 for Chinese Application No. 201810147665.3, with English language translation, 6 pages.
(Continued)

*Primary Examiner* — George Manuel

(57) ABSTRACT

A heart beat detection device comprises at least one optical reflection sensor to be positioned on the skin of a person. The sensor unit is provided with a light emitter and a corresponding light receiver which converts the light reflected by the skin into an electric signal and comprises electrically adjustable optical filters connected to the emitter, to the receiver or to both of them in order to select, upon operation, a desired light wavelength and perform processing of the signals thus obtained in order to reinforce the heart beat signal. A system with this device and a detection method are also described.

10 Claims, 3 Drawing Sheets

Related U.S. Application Data of application No. 15/789,220, filed on Oct. 20, 2017, now Pat. No. 10,285,602, which is a continuation of application No. 14/808,488, filed on Jul. 24, 2015, now Pat. No. 9,833,155, which is a continuation of application No. PCT/IB2014/058428, filed on Jan. 21, 2014.

(51) Int. Cl.
*A61B 5/0533* (2021.01)
*A61B 5/0531* (2021.01)

(52) U.S. Cl.
CPC .......... *A61B 5/0531* (2013.01); *A61B 5/0533* (2013.01); *A61B 5/7203* (2013.01); *A61B 5/7214* (2013.01); *A61B 2562/0219* (2013.01)

(58) Field of Classification Search
CPC ... A61B 5/0533; A61B 5/7203; A61B 5/7214; A61K 2300/00; A61K 31/138; A61K 31/185; A61K 31/194; A61K 31/285; A61K 31/29; A61K 31/65; A61K 31/704; A61K 31/7048; A61K 31/706; A61K 31/7068; A61K 33/24; A61K 33/243; A61K 33/245; A61K 33/36; A61K 38/00; A61K 45/06; A61K 9/0014; A61K 9/0019; A61K 9/0043; A61K 9/0046; A61K 9/0048; A61K 9/0053; A61K 9/007; A61P 35/00; A61P 35/02; C07K 14/4746; G01N 2333/4748; G01N 2500/00; G01N 33/5748; G01N 33/6848

See application file for complete search history.

(56) References Cited

U.S. PATENT DOCUMENTS

| | | | |
|---|---|---|---|
| 9,833,155 | B2 | 12/2017 | Tognetti et al. |
| 10,285,602 | B2 | 5/2019 | Tognetti et al. |
| 2003/0065269 | A1* | 4/2003 | Vetter .................... A61B 5/721 600/503 |
| 2003/0229276 | A1 | 12/2003 | Sarussi et al. |
| 2010/0113948 | A1 | 5/2010 | Yang et al. |
| 2010/0185068 | A1 | 7/2010 | Park et al. |
| 2010/0280402 | A1 | 11/2010 | Dunbar et al. |
| 2012/0190948 | A1 | 7/2012 | Vetter et al. |
| 2012/0271121 | A1 | 10/2012 | Della Torre et al. |

FOREIGN PATENT DOCUMENTS

| | | |
|---|---|---|
| CN | 101290309 A | 10/2008 |
| CN | 101533159 A | 9/2009 |
| CN | 101730503 A | 6/2010 |
| CN | 102781310 A | 11/2012 |
| EP | 2462866 A2 | 6/2012 |
| JP | 2007-105338 A | 4/2007 |
| JP | 2009-545356 A | 12/2009 |
| JP | 2010-119854 A | 6/2010 |
| WO | WO 2008/015598 A2 | 2/2008 |
| WO | WO 2011/150379 A2 | 12/2011 |
| WO | WO 2012/082749 A1 | 6/2012 |
| WO | WO 2014/115075 A1 | 7/2014 |

OTHER PUBLICATIONS

Non-Final Office Action dated Mar. 1, 2017 for U.S. Appl. No. 14/808,488, 7 pages.
Non-Final Office Action dated Jun. 12, 2018 for U.S. Appl. No. 15/789,220, 8 pages.
Examination Report No. 1 dated Dec. 21, 2016 for Australian Application No. 2014208391, 2 pages.
Examination Report No. 2 dated Jun. 23, 2017 for Australian Application No. 2014208391, 3 pages.
First Office Action dated Dec. 29, 2016 for Chinese Application No. 20140013880.4, 8 pages.
First Office Action dated Aug. 30, 2018 for Chinese Application No. 201810147665.3, 7 pages.
International Search Report and Written Opinion dated May 13, 2014 for International Application No. PCT/IB2014/058428, 6 pages.
Second Office Action dated Jul. 28, 2017 for Chinese Application No. 201480013880.4, with English translation, 10 pages.
Second Office Action dated May 7, 2019 for Chinese Application No. 201810147665.3, 7 pages.
Office Action dated Nov. 8, 2017 for Japanese Application No. 2015-554282, with English translation, 14 pages.
Office Action dated May 9, 2022 for Canadian Application No. 2,899,216, 3 pages.

* cited by examiner

DEVICE, SYSTEM AND METHOD FOR DETECTION AND PROCESSING OF HEARTBEAT SIGNALS

CROSS-REFERENCE TO RELATED APPLICATIONS

This application is a continuation of U.S. patent application Ser. No. 16/371,701, filed Apr. 1, 2019, which is a continuation of U.S. patent application Ser. No. 15/789,220, filed Oct. 20, 2017, now U.S. Pat. No. 10,285,602, which is a continuation of U.S. patent application Ser. No. 14/808,488, filed Jul. 24, 2015, now U.S. Pat. No. 9,833,155, which is a continuation of International Patent Application No. PCT/IB2014/058428, filed Jan. 21, 2014, which claims priority to and the benefit of Italian Patent Application No. MI2013A000104, filed Jan. 24, 2013, the disclosures of each of which are hereby incorporated by reference in their entirety.

The present invention relates to innovative devices, systems and methods for detecting the heart beat.

Heart beat detection systems (also called BVP—Blood Volume Pulse—detection systems) which function optically are known. These systems usually employ a light emitter which by means of reflection or transparency illuminates a suitable receiver after the emitted light has struck or passed through a zone of the body.

Basically, these heart rate monitors are detection systems which are able to measure the way in which the blood volume changes over time in a specific zone of the body.

Generally, the reflection devices are placed on a zone of the body, such as the wrist, where there is a variation in the quantity of light reflected depending on the superficial blood flow in this zone. The transparency devices are instead applied in the vicinity of relatively thin parts of the body (such as the fingers or the ear lobes) so that the light is able to pass through them and detect the variation the light passing through owing to the blood flow in said parts.

Both systems, however, subject to disturbances of the useful signal, for example due to both the surrounding light conditions and the movement of the person undergoing measurement.

For example, the sensor operates by means of contact with a deformable medium—the skin—inside which blood flows. This medium is subject to mechanical deformation which corrupts the measurement, adding an unwanted signal, namely noise.

Reflection devices are mere practical for prolonged use, but the variation in reflected light produced by the variations in blood flow following the heart heat is very small and moreover is generally affected by a large amount of noise.

For example, although the wrist is one of the most convenient positions for wearing a reflection sensor for detecting the pulse, the noise on the signal, created by the movement of the tissues underneath the sensor following, for example, the movement of the limb, the wrist or the fingers, is one of the major obstacles to optical detection of the pulse in this zone. Also the act of moving or walking produces relative movements of the sensor and tissues which produce further disturbances of a significant nature.

In the art various solutions have been proposed in order to try to improve the signal/noise ratio during reflection detection, attempting to filter the various disturbances superimposed on the useful signal.

For example it has been proposed using movement sensors arranged together with optical sensors for detecting relatively wide amplitude movements of the body to which the sensor is applied. This detection arrangement, however, does not provide data about the relative displacement of sensor and underlying tissue and is usually used to prevent reading of the optical sensor in the case of excessive movements on the part of the person, which it is assumed a priori may produce a large amount of disturbance which cannot be effectively filtered. In the case of prolonged physical activity, the sensor remains, however, deactivated for a long period and precisely when detection of the heart beat is of most interest.

It has also been proposed using two light sources with a suitable different wavelength.

The first wavelength has been chosen from among those wavelengths which are not absorbed by the oxyhaemoglobin (for example red), while the second wavelength is chosen from among those which are better absorbed by the oxyhaemoglobin (for example green). This results in a first signal which is better related to the movement of the tissues and a second signal which is better related to the blood flow. Filtering of the noise is then performed by suitably subtracting the first signal from the second signal, so as to mitigate the effect of the relative movements of tissues and sensor. Such a system is described for example in EP2462866.

A filtering system of this type provides an output signal with reduced noise. However, most often the signal/noise ratio is still very unfavourable. Moreover, not always does the response to the specific wavelength chosen remain constant with the passing of time and/or change of person undergoing the measurement.

Mixed methods also provide results which are not entirely satisfactory. For example, the noise is very high both when running and when working on a computer (finger movements). In the first case accelerometers are most useful for eliminating the noise, while in the second case it is preferable to make use of the system with two wavelengths. The simultaneous use of both methods as proposed in the prior art (for example, as described again in US2012150052) compensates, however, only for a number of noise sources and still does not provide a satisfactory signal/noise ratio for special applications or where the person is free to perform any daily activity. Moreover, the two systems may interfere with each other, further hindering detection.

A general object of the present invention is to provide a system able to ensure satisfactory detection of the heart beat even in the presence of disturbances caused by various sources. A further object is to provide an innovative system for processing heart beat signals.

In view of these objects the idea which has occurred, according to the invention, is to provide a heart beat detection device comprising at least one optical reflection sensor unit to be placed on the person's skin, the sensor unit being provided with a light emitter and a corresponding light receiver which converts the light reflected by the skin into an electric signal, characterized in that it comprises electrically adjustable optical filters which are connected to the emitter, to the receiver or to both of them in order to select, upon operation, a desired wavelength of the light.

The idea has also occurred to provide a system for detecting and processing physiological data, comprising at least one device according to any one of the preceding claims connected by means of a wireless interface to a data processing and transmission unit which receives the data from the device and processes it.

The idea has also occurred to provide a method for increasing the signal/noise ratio of an electric signal for detecting the heart beat optically by means of at least one optical refection sensor unit, comprising differentiating between the effects of at least two light wavelengths by means of electrically adjustable optical filters and processing the corresponding signals received from the at least one optical reflection unit in order to obtain the electric signal representing the heart beat.

As will become clear from the description and the drawings, according to the invention a device for detecting or monitoring the heart rate may comprise a sensor system which is in contact with the skin and which communicates with a central processing system. The remote system may comprise one or more optical detection systems for measuring the variations in blood volume making use of the physical principles of absorption and fluorescence. The optical systems may comprise:
- one or more wide-band light emitters (for example LEDs);
- one or more wide-band light receivers (for example photodiodes or phototransistors) and
- one or more tunable monochromators which can be connected to the light emitters, to the light receivers or to both of them, in order to select a certain wavelength.

The heart rate monitor may also comprise one or more of the following:
- one or more optical detection systems situated at a fixed distance along the direction of the blood flow in order to estimate the propagation time of the blood;
- an electrical detection system comprising two or more electrodes in contact with the skin for measuring the galvanic response of the skin, and
- a mechanical detection system for measuring the three-dimensional acceleration and the orientation of the system.

The heart frequency monitor may also envisage that one or more monohronaturs allow the optical detection system to work both in absorption mode and in fluorescence mode at two car more wavelengths.

Still according to the method for maximizing the signal/noise ratio of the blood volume signal may comprise the steps of:
- differentiating between the effects of two (or more) wavelengths in absorption mode and fluorescence mode on signals of the optical detection systems;
- dynamically tuning the two (or more) wavelengths in order to maximize the signal levels of the optical detection systems.

Moreover the method may comprise one or more of the following steps:
- combining the effects of the absorption mode and fluorescence mode on the signals of the optical detection systems;
- combining the signals from the optical detection systems with the signal of the electrical detection system;
- eliminating the effect of deformation of the medium on the blood propagation time, and
- eliminating the effect of deformation of the medium resulting from other mechanical effects which are contained in the signal supplied by the mechanical detection system The heart rate monitor may also comprise a remote system in contact with a user's skin and communicating with a central processing system.

The remote system may also comprise one or more of the following elements:
- a remote processor;
- a detection system connected to the remote processor;
- a remote memory connected to the remote processor;
- a clock signal generator connected to the remote processor;
- a remote user interface connected to the remote processor;
- a remote transceiver connected to the remote processor;
- a remote antenna connected to the remote transceiver, and
- a remote battery connected to the remote processor, to the detection system, to the remote memory, to the clock signal generator, and to the remote transceiver.

The central processing system may comprise:
- a central processor;
- a central memory connected to the central processor;
- a central transceiver connected to the central processor, and
- a central antenna connected to the central transceiver.

The said central memory may further comprise a set of instructions which can be carried out on the central processor, the instructions comprising:
- an algorithm for maximizing the signal/noise ratio of the blood volume signal received from the remote system, and
- an algorithm for processing the optimized blood volume signal for determining a pulsation signal based on detection of the peak value.

In order to illustrate more clearly the innovative principles of the present invention and its advantages compared to the prior art, examples of embodiment applying these principles will be described below with the aid of the accompanying drawings. In the drawings.

Figure 1:
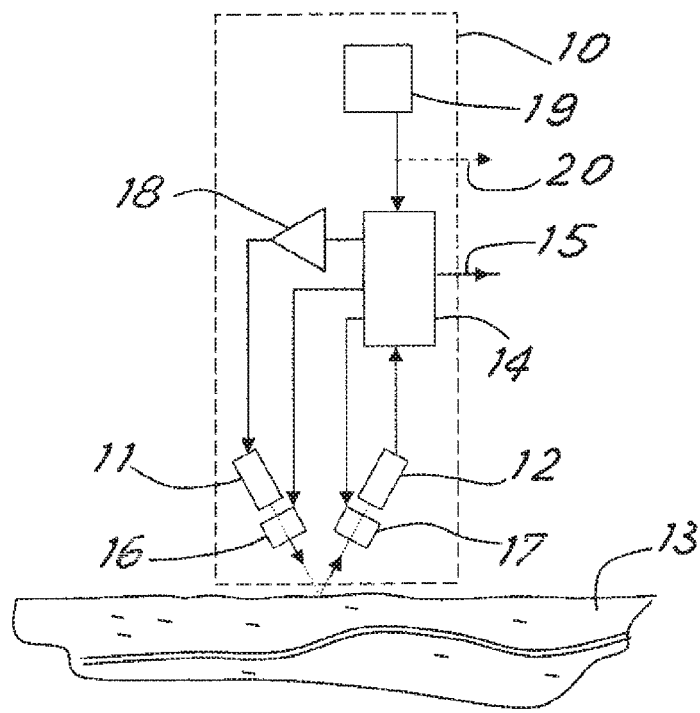
FIG. 1 shows a block diagram of a first reflection detection device provided in accordance with the principles of the present invention.

With reference to the figures, FIG. 1 shows a first reflection detector according to the invention for detecting the heart beat.

Such a detector, which is generally denoted by 10, comprises a light emitter 11 (for example an LED diode emitter) and a corresponding receiver 12 (for example a photodiode or phototransistor) which receives the light of the emitter 11 after reflection on the skin 13 of the person undergoing heart beat detection. Advantageously, as will be clarified below, the detector or device 10 may be positioned on the rear part of the wrist, for example in the manner of a wrist-watch.

The receiver 12 converts the light received into an electric signal sent to an electronic processing block 14 which emits a corresponding signal 15 (also called BVP—i.e. Blood Volume Pulse—signal) which depends on the heart beat of the person. The block 14 may be a combination of an analog amplification circuit and programmable microprocessor device for processing a signal, as may be easily imagined by the person skilled in the art in the light of the description provided here.

Advantageously, the emitter 11 emits light in a wide spectrum (for example white light) and the device 10 comprises an adjustable optical filter 16 and/or an adjustable optical filter 17, which are arranged respectively in front of the transmitter 11 and the receiver 12. These optical filters may be controlled by the processing block 14 so as to be tuned to a desired wavelength for filtering the light sent and/or reflected.

Advantageously, these optical filters comprise so-called "monochromators" and allow dynamic selection of a specific wavelength from a wide-spectrum light. In particular, it has been found to be advantageous to use tunable Fabry-Perot monochromoators, known per se, which can be easily miniaturized.

Again advantageously, the device may comprise a circuit 18 for powering the emitter 11 which is controlled by the processing block 14 so as to tune the emission luminosity of the emitter 11 to a desired value.

For reasons which will become clear below, the device 10 may also comprise a known accelerometer 19 which sends movement signals to the processing block 14. Advantageously, the accelerometer is chosen to measure the three-dimensional acceleration and the orientation of the system.

As is known, the oxyhaemoglobin present in the blood absorbs given wavelengths. This effect is referred to as "absorption".

Moreover, the oxyhaemoglobin re-emits part of the energy absorbed in the form of light at a wavelength different from that absorbed. This effect is referred to as "fluorescence".

Owing to the use of adjustable filters, it is possible to configure the system in order to make use first of one effect and then the other effect. In the first mode the wavelength which maximizes absorption is provided and the same wavelength is "observed" by means of the receiver 12. In the second mode the wavelength which maximizes the fluorescence is provided and the fluorescence wavelength characteristic of oxyhaemoglobin (wavelength which is always greater than the incident wavelength for energy balance reasons) is observed by means of the receiver 11.

By combining the signal read by the receiver in the two different modes, i.e. "absorption" mode and "fluorescence" mode, it is possible to improve the signal/noise ratio.

Moreover, owing to the adjustability of the filters it is possible to adapt the fluorescence and/or absorption wavelength to the characteristics of the skin of the person whose heart beat is being detected (for example age, degree of tanning, skin complexion, presence of fat, presence of hair).

In fact the skin situated between detector and oxyhaemoglobin creates optical interference which may alter the light emitted and/or received. Therefore, it has been found useful to attempt to find, possibly whenever the device is switched on, the wavelengths which maximize the amplitude of the BVP signal, depending on the characteristics of the skin, both in fluorescence mode and in absorption mode.

For example, extremely fair skin favours the penetration of light and therefore, in absorption mode, wavelengths close to the UV hand may be effectively used. On the contrary, tanned or dark skins do not allow small wavelengths to reach the receiver except in the case where the intensity is such that it adversely affects the battery life.

A similar situation exists in fluorescence mode, where a maximum response of the oxyhaemoglobin is obtained by performing stimulation in the violet-blue band and detection in the orange band.

In other words, during operation, the processing block 14 may tune the filters to wavelengths considered suitable for detecting the heart beat using the "absorption" method (for example in the range of 530-580 nm for dark skin and 410-450 nm for extremely fair skin) and acquire the corresponding signal reflected and captured by the receiver 12. The processing block 14 may also tune the filters to a wavelength considered suitable for detecting the heart heat using the "fluorescence" method (for example in the range 410-450 nm for the emission filter and 590-630 nm for the reception filter) and acquire the corresponding fluorescence signal captured by the receiver 12. By superimposing the two signals received (suitably compensating for the temporal delay between the two measurements) it is possible to obtain a BVP signal with a greater amplitude than the background noise.

Moreover, during the two measurements (or, advantageously, during a calibration step Which may take place upon switching on the device following application onto the skin, or cyclically during operation) the device may vary the wavelength of the filter in the region of the basic wavelengths defined for fluorescence and absorption, attempting to maximize the signal peak received in the two modes. After defining the wavelengths for which the greater signal is obtained, the device may use these wavelengths for the subsequent measurements until the subsequent calibration operation is performed.

By periodically repeating calibration during operation of the device it is possible to compensate also for the varying conditions of the skin (for example, variation in the degree of tanning, sweating or change in temperature) which may influence the measurement.

By way of a further advantage it is also possible to compensate for disturbances on the signal due to relative movements of the skin and device, for example caused by movements of the person or movements of the muscles and tendons of the body zone on which the sensor is placed (for example movement of the fingers). In fact it is possible to tune the filter (or filters, in the case of a device with both filters) so that the light emitted by the emitter 11 is characterized by a wavelength which is less sensitive to flowing of the blood, but more sensitive to movements on or under the skin (for example the wavelength 650-750 nm). The corresponding signal captured by the detector 12 may be used by the processing block 14 as a noise signal to be subtracted from the electric signal obtained by the detection of the BVP signal, via an adaptive numerical filter, so as to eliminate an important noise component.

Filtering may also take place for selecting green light or red light for the uses substantially of the prior art or also for filtering (using suitable emitters) in the infrared range or other ranges.

Advantageously, the detector 10 may also use the signal supplied by the accelerometer 19 in order to compensate for disturbances due to major movements of the device (for example, as a result of physical activity performed by the person). The accelerometer signal may be supplied to the block 14 in order to provide an adaptive numerical filter which intervenes in the case of sudden accelerations (for example when running).

The signal of the accelerometer 19 may also be used to prevent emission of the BVP signal by the device when the acceleration detected is above a threshold which has been determined beforehand as corresponding to a movement noise source which is too great for effective compensation of the noise on the BVP detected by the optical system.

In order to reduce the noise on the output signal, the device 10 may also advantageously act on the luminous intensity of the light emitted by the sensor 11. However, in the case of battery-powered devices, a greater light intensity may negatively affect the duration of the battery charge.

Figure 2:
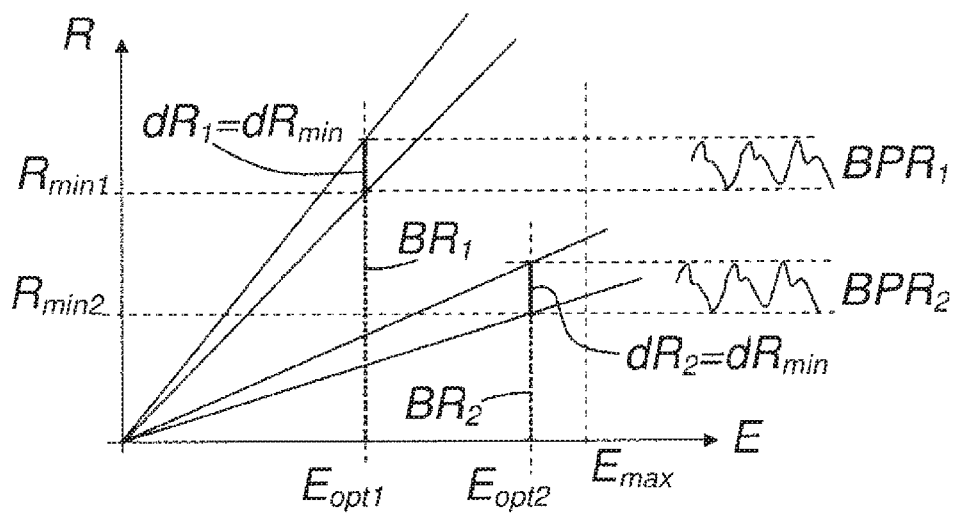
FIG. 2 shows a graph of signals detected by an apparatus according to the invention.

FIG. 2 shows a graph which schematically illustrates the relationship between light E emitted by the emitter (axis X) and amplitude of the signal received R (axis Y).

As can be seen from the graph, there exists essentially a linear relationship between light emitted and reflected light measured by the receiver. The noise signal, or BR (Background Reflection) signal, which may also comprise any ambient light captured by the sensor, and the BPR (Blood Pulse Reflection) signal are therefore both incremented with an increase in the luminous emission intensity E. The slope of the two straight lines in the graph, which define the light reflection curve, may vary from person to person.

All the above means that, given a certain emitted light E, a first person may have a certain dR (namely a certain amplitude dR of periodic variation of reflected light which carries blood pulsation information). A second person may have, for the same value E, a value dR smaller or greater than the value dR of the first person.

If a value dRmin is established (namely a minimum useful signal value received) the emitter will be advantageously controlled by the block 14 so as to have in any case emission E which allows the signal dR to be kept above the value dRmin. Although it is possible to emit constantly a light at a value (for example, 100 med) which ensures that this condition always exists, such a solution may result in an unnecessary premature wear of the battery power.

Advantageously, it is instead preferable that the signal dR should always be only slightly higher than the value dRmin. A value of E, which may be called Eopt (i.e. E optimum), is thus obtained, this value satisfying this condition and being variable depending on the person to another or different conditions of the person. An this is shown by way of example in FIG. 2 (where Eop1 and Eopt2 give rise to the same $dR_1=dR_2=dRmin$ for two sample persons).

The block 14 may therefore advantageously vary the emission E by means of the power supply element 18 as mentioned above so as to keep the signal dR slightly above dRmin (optionally with a small safety margin) so as to optimize the amplitude of the useful signal, maximizing at the same time the battery life.

It is thus possible to rise high-luminosity emitters (LEDs) also in battery systems, using the higher light emissions only in the case of need and only for the time needed.

The power supply of the sources may also be provided pulsed and/or alternating between the emitters, both in order to reduce the battery consumption and so as to share part or all of the drive circuit among the emitters.

Figure 3:
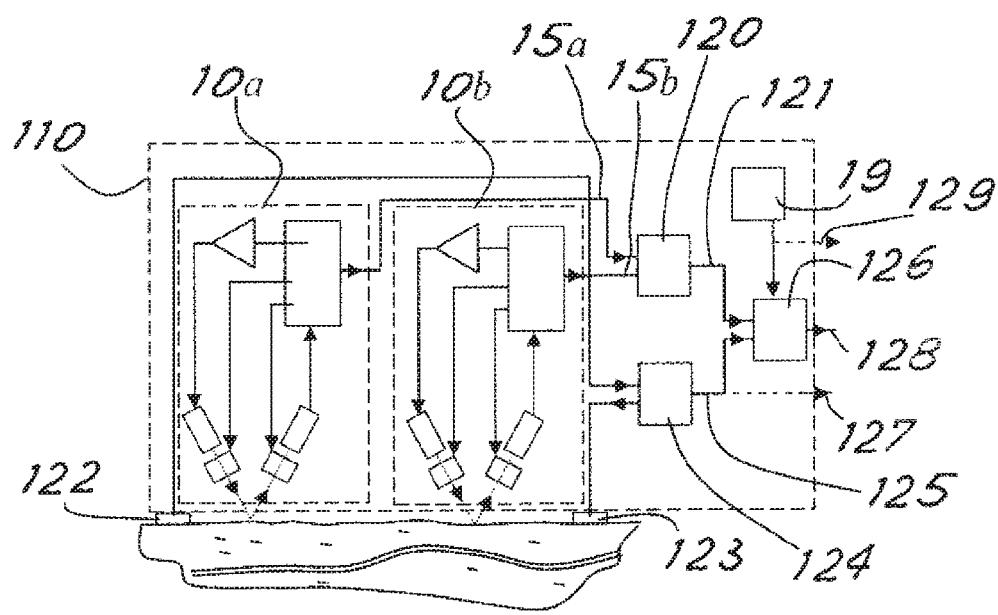
FIG. 3 shows a block diagram of a second reflection detection device provided in accordance with the principles of the present invention.

FIG. 3 shows a second embodiment of a detector according to the invention. In this second embodiment, which is denoted overall by 110, two detectors or devices 10, as described above, denoted by 10a and 10b, are used, the BVP signal outputs 15a and 15b thereof being further processed by a processing and comparison block 120.

The two detectors 10a and 10b are arranged with the corresponding optical units (formed by emitter 11, receiver 12 and any optical filters 16 and/or 17) arranged generally along the main direction of flow of the blood in the part of the body where the device 110 is positioned. For example, in the case of positioning on a limb, the direction will be along the axis of the limb itself. In particular, in the case of positioning on a wrist, the direction may be advantageously that of elbow-to-hand.

The distance between the optical units may be a few centimetres or even less, also depending on the sensitivity of the detector and the position chosen on the body.

Figure 4:
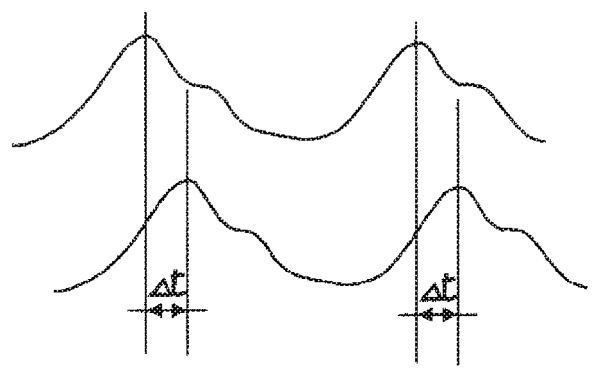
FIG. 4 shows a further graph illustrating signals detected by an apparatus according to the invention.

Owing to the use of the two devices 10a and 10b, two signals 15a and 15b which are slightly phase-displaced in relation to each other (depending on the mutual distance) will be obtained, as shown schematically in FIG. 4.

By means of calculation of the correlation, upon variation of the time of the two signals, performed by the block 120, it is possible to calculate the time "delta-t" for transit of the blood between the two optical units.

By detecting the variations of this time (or the apparent speed of displacement of the blood between the two optical units) it has been found to be possible to obtain information about the movement of the tissues underneath and between the two optical units. In other words it has been found that these movements vary the length of the blood vessels and therefore alter the speed value detected or, rather, the transit time between the two optical units (which are at a fixed distance from each other).

It is thus possible to obtain further information about the noise which has been produced by the muscular movement and which may be subtracted from the BVP signal, obtaining an improved BVP signal at the output 121 of the processing block 120.

Advantageously, the device 110 also comprises a system for measuring the conductivity of the skin, preferably in the ventral zone of the wrist, which has a pronounced electrodermal activity.

The system for measuring the conductivity (or the galvanic effect of the skin) comprises advantageously two metal electrodes 122, 123 which make contact with the skin in the chosen zone and are connected to a measurement block 124 which detects the electrical resistance between the two electrodes.

The measurement of the resistance may be simply performed by causing a low or very low strength current to flow across the skin. A compensation algorithm may also be used to control the current which flows through the skin so as to balance a base line for the person, taking it as a zero line. In order to avoid polarization and/or electrolysis phenomena, the power supply on the electrodes may be periodically inverted. Moreover, the electrodes may be silver-lined so as to prevent possible damage to the skin and deterioration of the electrode.

The inversion of polarity drastically reduces the risk of deposition of Ag+ ions on the outer layers of the skin. The ions which may have been deposited on the skin are combined again with the surface of the electrode after each inversion of polarity.

The resistance value measured by the detector is present on the output 125 of the block 124 and is sent to a further processing block 126 which performs further processing of the BPV signal 121 so as to reduce further the noise associated with it, using variations in the conductivity at the output 125

In fact it has been found that the variation in conductivity measured on the skin in the region of the optical unit has a progression similar to the BVP added to the slow progression of sweating. The variation in conductivity observed, similar to the BVP, is due in particular to the wave of blood which travels along superficial vessels and which tends to constrict the sweat glands, which release small amounts of fluid at the same frequency as the heart beat.

This signal is in general very small and cannot be easily used alone to obtain an indication of the heart beat, but if combined with the signal detected optically as described above, allows a further improvement in the signal/noise ratio of the BVP signal output by the device according to the invention.

Even though not shown in FIG. 1, this system for measuring the conductivity may be used in the same way also to reduce the noise in the device 10 according to FIG. 1, using a processing block 125, to the input of which the signal 15 of the block 14 is sent (instead of the signal 121 of the block 120), as may be now easily imagined by the person skilled in the art.

The slow variation in the conductivity of the skin may also be sent outside of the device 110 (or the device 10 which uses such a conductivity detector) in order to be used to provide further physiological information about the person, as is indicated by way of example by a broken line 127 in FIG. 3.

The device 110 may also use accelerometer 19 as described for the device in FIG. 1. The accelerometer is in this case advantageously connected to the last processing block 126 which is positioned before the BVP signal output 128 of the device. In both the devices 10 and 110, the three-dimensional acceleration signal may also be sent externally so as to used to provide further information about the person, as indicated by way of example by the broken lines 20 and 129 in FIGS. 1 and 3.

Figure 5:
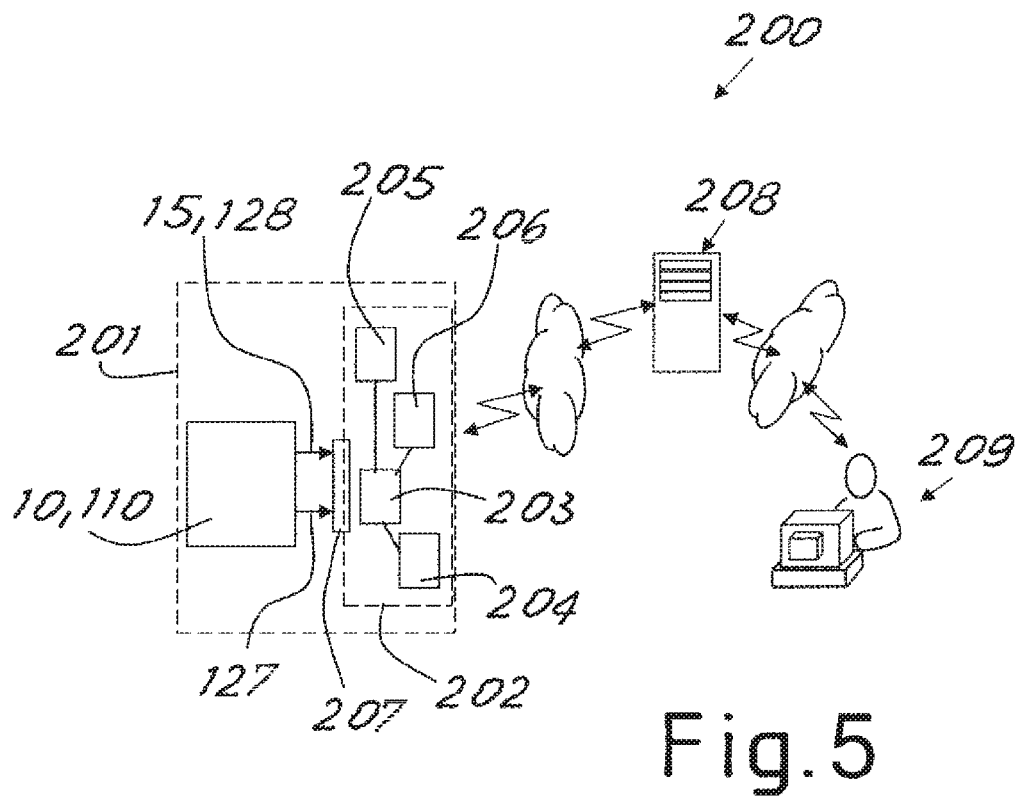
FIG. 5 shows a block diagram of a possible system for remote processing of the data detected by the sensors according to the invention.

FIG. 5 shows schematically an advantageous complete system, indicated generally by 200, for detecting and processing the physiological data of a person.

The system 200 comprises a remote device 201 which comprises in turn a detector of the same type as the detector 10 or 110 described here, the BVP signals (15 or 128) and any conductivity signal 127 of which are sent to a data processing and transmission unit 202.

This unit 202 is advantageously formed as a microprocessor unit which is suitably programmed and therefore comprises advantageously a processor 203 which receives the signals from the device 10, 110, a program memory 204, a data memory 205 and a transmitting unit 206 which are connected to the processor 203.

The unit 202 may be incorporated in the remote device 201 or be entirely or partly designed as a separate device and may also comprise known systems for introducing commands and for displaying data and information (for example by means of a touch-screen display).

The unit 202 may be designed to communicate (advantageously via a wireless or mobile phone connection for connection to the Internet) With a remote server 208 which may in turn be in communication with one or more terminals 209.

In this way the physiological data processed or preprocessed by the device 201 may be sent (also after further processing by the server 208) to a remote display and control terminal 209. A remote examination of a person wearing the device 201 is thus possible. The data processed by the server (or also by the remote terminal 209 upon operation by an operator) may be sent to the unit 202 for local display, for example, by the said person on whom the measurement is being performed.

The signals 15, 128 and 127 may be sent directly to the unit 202 or pass via a communication interface 207 known per se (of the cabled or advantageously wireless type).

In the case of a wireless connection, the detector 10, 110, together with the suitable communication interface 207, may be incorporated in a small portable device (for example in the form of a wrist-watch) which communicates wirelessly with the processing and communication unit 202, kept in a pocket or hand-held.

Figure 6:
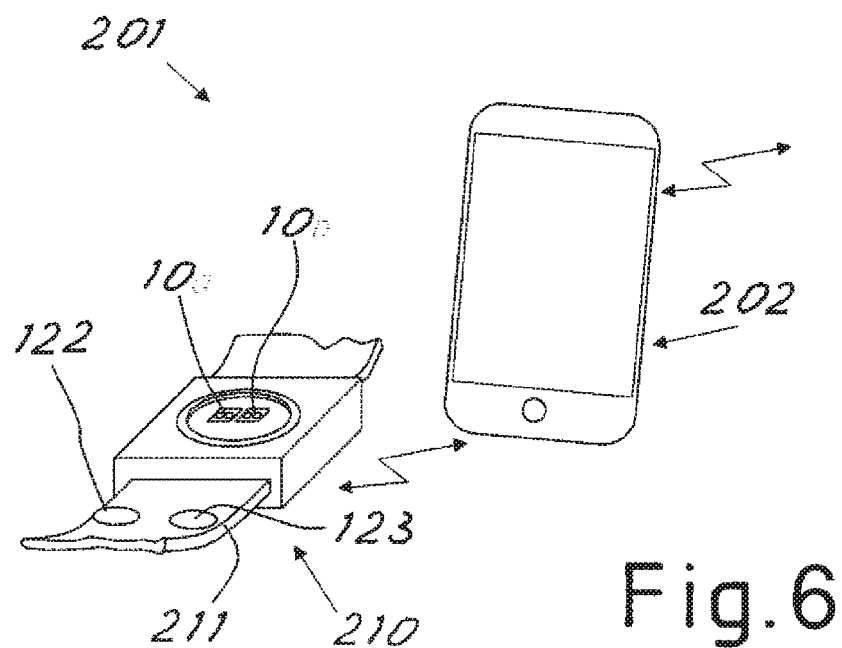
FIG. 6 shows a schematic view of a bracelet detection system and intelligent portable terminal for processing (or initial processing) of the signals detected.

FIG. 6 shows an advantageous embodiment of the device 201 according to FIG. 5. In this embodiment the detector 10, 110 is designed in the form of a device 210 to be worn on the wrist, with the optical sensors arranged on as side intended to be placed in contact with the skin when the device is fastened to the wrist by means of a strap 211. Preferably, the electrical sensors are arranged on the strap itself. Advantageously, a sealing ring 212 may be provided around the optical sensors and is pressed against the skin and prevents the entry of ambient light and/or external moisture into the area monitored by the sensors.

The device 210 communicates wirelessly (for example via the interface 207 advantageously of the low energy Bluetooth type) with an intelligent terminal (such as advantageously a smart phone or a tablet) which, by means of suitable programming, which may be now easily imagined, performs the functions of a processing and communications unit 202. The terminal may in turn communicate with the Internet or mobile phone network wirelessly as mentioned above, in the case where remote processing or display of the data is required.

The input of commands and display of information locally may be easily performed by means of a touch screen 213 of the terminal 202.

An interesting application of the system shown in FIGS. 5 and/or 6 may be that of indicating to the person wearing the device 210 and/or to a remote operator via the terminal 209 various physiological parameters such as the stress state, the level of physical activity and physical condition, the quality of sleep, the excitation level, etc. These parameters may be determined on the basis of the signals detected by the device 210. The operator may also receive the data from a plurality of remote detectors worn by several persons.

At this point it is clear how the predefined objects have been achieved. Using the methods and the devices according to the invention it is possible to obtain precise and reliable signals in many conditions where there is disturbance. For example, it is possible to change the operating mode of the system, choosing the colour of the light depending on the external conditions and the condition and the type of skin, while also switching between absorption mode or fluorescence mode.

A heart rate monitor according to the invention may advantageously comprise a sensor system in contact with the skin and communicating with a central processing system. Moreover, the sensor system may comprise one or more optical detection systems for measuring the variations in the blood volume using the physical principles of absorption and/or fluorescence. The optical systems advantageously comprise one or more wide-band light emitters (LEDs) and one or more wide-band light receivers and one or more tunable monochromator filters which are connected to light emitters, light receivers or both of them, in order to select a certain wavelength.

Owing to the principles of the invention, if required, it is possible to remove the effect of deformation of the tissues on the blood propagation time. The propagation speed is altered partly by the beat itself, but more so by stretching of the tissues. By making suitable use of the signal obtained by means of the system described it is possible to remove a further noise component. Moreover, if required, it is possible to remove the effect of the "macroscopic" movement measured by the accelerometers. It is also possible to use effectively high-luminosity emitters.

Obviously the description provided above of embodiments applying the innovative principles of the present invention is provided by way of example of these innovative principles and must therefore not be regarded as limiting the scope of the rights claimed herein.

For example, the various processing blocks described above as separate may also be combined with each other in a single processing block (for example a suitably programmed microcontroller unit) as may now be easily imagined by the person skilled in the art. For example, the block 14 of the detector 10 or the two detectors 10*a* and 10*b* may also be designed as a single processing block, which may also comprise the block 120 and, possibly, the blocks 124 and 126. Advantageously, the various blocks may be realized by means of algorithms which comprise at least one of the following: an algorithm for controlling the optical detection systems and receiving signals from the optical detection systems during the absorption mode; an algorithm for controlling the optical detection systems and receiving signals from the optical detection systems during the fluorescence mode; an algorithm for controlling the system for detection of the electrical conductivity of the skin and receiving signals from the system for detecting the electrical conductivity of the skin; an algorithm for controlling the system for detecting the acceleration (or mechanical movement) and receiving signals from the acceleration detection system.

These algorithms may be realized by means of a suitable program which can be performed by the processor contained in the device according to the invention, as may be imagined by the person skilled in the art on the basis of the present description. Advantageously, the filters may be all adaptive numerical filters.

In the case of remote transmission it is also possible to envisage an algorithm for encoding signals received from the detection device or devices, for transmission thereof via the transceiver of the device to the external processing unit, and an algorithm for decoding signals received via the transceiver from the external processing unit. Further program parts may manage status commands for controlling a status light emitter (for example an LED) on a user interface of the device.

Thanks to the system which uses selectable filters for the wavelengths of the light, it is also possible to use, compare and process signals obtained at more than two wavelengths (for example blue, green, infrared) in order to optimize particular aspects of the detection operation.

The various innovative solutions according to the present invention which are described as being incorporated simultaneously in the examples of embodiment described above, may also be used separately in devices and systems according to the invention or may be differently combined.

The device according to the invention (for example in its device configuration 210) may also comprise further elements useful for practical operation such as a three-colour status light emitter (LED) connected to the processor for indicating the system status and a pushbutton connected to the remote processor for interacting with the detection device. The status indicated by the status indicator may be at least one of the following: battery power low, battery charging, data acquisition mode. The device may also comprise a port for recharging an internal battery.

The invention claimed is:

1. A heart beat detection device, comprising:
   at least one optical sensor unit configured to be placed near a skin of a person, the at least one optical sensor unit including:
   a light emitter configured to emit light onto the skin;
   a light receiver configured to receive light reflected by the skin and to convert the light reflected by the skin into an electric signal; and
   at least one optical filter configured to be tuned to one or more wavelengths of light to enable filtering of the light emitted by the light emitter and filtering of the light reflected by the skin, and operate in a first mode providing light having a wavelength that maximizes absorption by oxyhaemoglobin and a second mode providing light having a wavelength that maximizes fluorescence by oxyhaemoglobin.

2. The heart beat detection device according to claim 1, wherein the at least one optical filter comprises a Fabry-Perot monochromator.

3. The heart beat detection device according to claim 1, further comprising a processing unit configured to control the at least one optical filter to operate in the first mode or the second mode to determine a heart rate of the person.

4. The heart beat detection device according to claim 1, further comprising a processing unit configured to receive the electric signal from the light receiver and control the at least one optical filters to optimize an amplitude of the electric signal received.

5. The heart beat detection device according to claim 1, wherein the at least one optical sensor unit includes two optical sensor units arranged at a distance from each other and connected to a signal processing unit for estimating a blood propagation time between the two units, the signal processing unit modifying the signal detected by the at least one optical sensor unit depending on a variation in the blood propagation time.

6. The heart beat detection device according to claim 1, further comprising an electrical detection system for measuring a galvanic response of the skin and a processing unit configured to obtain a signal based on the galvanic response and to combine the signal based on the galvanic response with the electric signal.

7. The heart beat detection device according to claim 1, further comprising a device for measuring the acceleration of the heart beat detection device and a processing unit configured to modify the electric signal based on the acceleration.

8. The heart beat detection device according to claim 1, comprising a power supply element configured to receive a command from a processing unit for processing the electric signal and to vary a luminosity of the light emitted by the light emitter such that the electric signal is above a predefined minimum threshold.

9. The heart beat detection device according to claim 1, wherein the at least one optical filter includes:
   a first optical filter arranged in relation to the light emitter and configured to filter the light emitted by the light emitter to provide light having a wavelength within a specific range of wavelengths; and
   a second optical filter arranged in relation to the light receiver and configured to filter the light reflected by the skin such that the light receiver receives light having a wavelength within a specific range of wavelengths.

10. The heart beat detection device according to claim 1, further comprising a processing unit configured to:
    receive a first electric signal from the light receiver converted from light reflected by the skin when the heart beat detection device operates in the first mode in which the at least one filter is tuned to a range of wavelengths that maximizes absorption by oxyhaemoglobin;
    receive a second electric signal from the light receiver converted from light reflected by the skin when the heart beat detection device operates in the second mode in which the at least one filter is tuned to a range of wavelengths that maximizes fluorescence by oxyhaemoglobin; and combine the first electric signal and the second electric signal to improve a signal/noise ratio for determining a heart beat of the person.

\* \* \* \* \*